United States Patent
Vija (10) Patent No.: US 9,364,192 B2
(45) Date of Patent: Jun. 14, 2016

(54) ERROR ESTIMATES IN QUANTITATIVE FUNCTIONAL IMAGING

(71) Applicant: Siemens Medical Solutions USA, Inc., Malvern, PA (US)

(72) Inventor: Alexander Hans Vija, Evanston, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 178 days.

(21) Appl. No.: 14/202,116

(22) Filed: Mar. 10, 2014

(65) Prior Publication Data

US 2014/0270443 A1    Sep. 18, 2014

Related U.S. Application Data

(60) Provisional application No. 61/788,059, filed on Mar. 15, 2013.

(51) Int. Cl.
*G06K 9/00* (2006.01)
*A61B 6/00* (2006.01)
*A61B 6/03* (2006.01)

(52) U.S. Cl.
CPC .......... *A61B 6/5258* (2013.01); *A61B 6/037* (2013.01); *A61B 6/032* (2013.01); *A61B 6/5205* (2013.01); *A61B 6/582* (2013.01)

(58) Field of Classification Search
CPC ............. G06T 2207/10072; A61B 6/037; A61B 6/481
USPC ........................................... 382/131
See application file for complete search history.

(56) References Cited

U.S. PATENT DOCUMENTS

| | | | |
|---|---|---|---|
| 6,950,494 B2 | 9/2005 | Vija et al. | |
| 7,473,900 B2 | 1/2009 | Vija | |
| 7,526,060 B2* | 4/2009 | Ziegler | G06T 11/006 378/4 |
| 7,783,092 B2* | 8/2010 | Agam | G06T 7/0012 382/128 |
| 8,184,876 B2 | 5/2012 | Vija et al. | |
| 8,350,222 B2 | 1/2013 | Vija et al. | |
| 8,577,103 B2 | 11/2013 | Vija et al. | |
| 2008/0056550 A1* | 3/2008 | Kadir | A61B 6/037 382/131 |
| 2008/0075344 A1* | 3/2008 | Nambu | A61B 6/463 382/131 |
| 2009/0110256 A1* | 4/2009 | Thielemans | A61B 6/032 382/131 |
| 2009/0208075 A1* | 8/2009 | Fischer | G06T 7/0081 382/128 |
| 2010/0046818 A1* | 2/2010 | Yamaya | G01T 1/1648 382/131 |
| 2011/0044524 A1* | 2/2011 | Wang | G01R 33/54 382/131 |
| 2011/0164801 A1* | 7/2011 | Gagnon | G01R 33/481 382/131 |
| 2012/0326034 A1* | 12/2012 | Sachs | G06T 11/005 250/336.1 |

* cited by examiner

*Primary Examiner* — Bhavesh Mehta
*Assistant Examiner* — Ian Lemieux
(74) *Attorney, Agent, or Firm* — Peter Kendall (57) ABSTRACT

Systematic error is estimated as a function of location in quantitative functional imaging. The systematic error is estimated by perturbing the system matrix. The values of one or more variables of the system matrix are altered, and the reconstruction repeated. The differences in the resulting object or image data of the different reconstructions provide systematic error information as a function of location.

20 Claims, 2 Drawing Sheets

ERROR ESTIMATES IN QUANTITATIVE FUNCTIONAL IMAGING

RELATED APPLICATIONS

The present patent document claims the benefit of the filing date under 35 U.S.C. §119(e) of Provisional U.S. Patent Application Ser. No. 61/788,059, filed Mar. 15, 2013, which is hereby incorporated by reference.

BACKGROUND

The present embodiments relate to quantitative functional imaging. In particular, error information is provided for quantitative functional imaging.

Functional imaging includes positron emission tomography (PET), single photon emission computed tomography (SPECT), or other nuclear imaging. PET uses a detector ring about a patient to detect pairs of gamma rays emitted due to a collusion of a positron with an electron. The positron is generated by a radionuclide (tracer or radio-pharmaceutical) introduced into the patient. SPECT also uses introduction of a radioisotope (tracer or radio-pharmaceutical). A gamma camera is rotated about the patient to detect gamma rays emitted by the radionuclide. Both PET and SPECT provide 3D or 4D functional information, or information about uptake or other physiological function labeled by the tracer. This information is depicted in a volume image comprised out of intensity voxels typically in units of counts. The larger the intensity, the larger the uptake in the spatial region at the location of that voxel. However, this is only a relative measure, as the amount of activity concentration (activity per unit volume or activity per unit volume per unit time) has not been derived.

For quantitative functional imaging, the image now represents an estimate of the amount of uptake or activity concentration measured in units of Bq/ml or Bq/ml/s. However, any measurement has an associated error or uncertainty due the measurement method, including instrument limitations. Any error is comprised of statistical error and systematic error, which with known methods of propagation of error results in the total absolute error. The error itself may only be estimated, and that estimate itself has an associated error.

BRIEF SUMMARY

By way of introduction, the preferred embodiments described below include methods, systems, and non-transitory computer readable media for estimating error in quantitative functional imaging. The absolute error in a resulting quantitative functional image is estimated as a function of location. The values of one or more variables of the system matrix or image formation model are altered, and a reconstruction is repeated. The differences in the resulting object or image data of the different reconstructions provide systematic error information as a function of location. Statistical error or other sources of systematic and/or statistical error in the image formation model (e.g., detected data, system physics, isotope properties, and/or biological properties) may be determined.

In a first aspect, a method is provided for estimating error in quantitative functional imaging. A functional imaging system estimates activity concentration as a function of locations of an injected radio-pharmaceutical in a patient. A processor calculates systematic errors of the activity concentration as a function of the locations for the patient. The systematic error for at least one location is different than the systematic error for another location. The systematic errors are output.

In a second aspect, a non-transitory computer readable storage medium has stored therein data representing instructions executable by a programmed processor for estimating error in quantitative functional imaging. The storage medium includes instructions for first reconstructing an object from detected emissions in nuclear imaging as a function of a system matrix, altering the system matrix, second reconstructing the object from the detected emissions as a function of the altered system matrix, calculating a distribution of errors in space as a function of a difference of the object of the first reconstructing and the object of the second reconstructing, the error for one of the locations being different than for another of the locations, and generating an image of the distribution of the errors.

In a third aspect, a system is provided for estimating error in quantitative functional imaging. A single photon emission computed tomography scanner is configured to reconstruct with a system matrix and detected data. A processor is configured to vary a value of one or more variables of the system matrix and calculate systematic errors as a function of location from outputs of reconstructions with the system matrix with the various values of the one or more variables.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A spatially varying error, in two, three, or four dimensions, is estimated for the image formation process, seeking to estimate the activity concentration in-vivo using emission tomography. The principle may be expanded to any tomography, if the imaging physics are known. Knowing the error (e.g., tolerance) distribution in multiple dimensions (e.g., error map) may assist in diagnosis, treatment planning, and treatment follow up using the quantitative functional imaging and may improve the confidence in decision making. For instance, the error map indicates regions of low and high error, and thus a physician may assess if a tumor in deed changed in a statistically significant amount after treatment or not. An error map may also be used to estimate spatially varying internal radiation burden or in general assist in personalized internal dosimetry. Finally, treatment plan changes may be indicated or contra indicated depending on an assessment of the functional uptake and its associated error.

The source of the measurement error in emission tomography may be subdivided into four general groups according to the source of the error: i) biological distribution of the tracer in-vivo, ii) isotope property and its decay, iii) detection on the emitted radiation, and iv) data processing. Generally, there are statistical and systematic errors. The errors may either be correlated or not. In some cases, the underlying statistical distribution function is known. In other cases, the distribution is estimated. For instance, for the physical process of the isotope decay the underlying statistics is Poisson, which also is an example of an uncorrelated error. However, in most cases, a Gaussian or normal distribution is a good and sufficient assumption. Due to the central limit theorem, the error distribution tends to become normally distributed in the limit of large samples. A systematic error is typically associated with the measurement method itself and also has an underlying statistical distribution.

The error estimation methods for the four different sources of error i)-iv) as described above share a common technique for determining the error. The input variable or data consistent with the physics process, including chemical and biological, is perturbed or changed. The so modified input data is propagated through the respective component of the image formation chain or even the entire image formation chain to ascertain the resulting difference in the image compared to the image using the measured data without the change.

The actual measured data itself is in fact only one realization of many possible realizations consistent with the physics of that process. One example is the item ii) of isotope decay. The physical process of isotope decay gives rise to a statistical process defined as Poisson statistics. When some isotope of with a half-life of $T_{1/2}$ decays, the isotope emits dN particles in a time interval dT. An ideal detection system with efficiency eta=1 may be assumed. The measurement system measures dN particle detections for the time interval T, resulting in $M_0$ counts. If the same measurement is repeated, the measurement would yield $M_1$ counts. $M_0$ and $M_1$ are two realizations of the same experiment. From physics, the variance of the $1^{st}$ measurement yielding the value $M_0$ is also $M_0$, the error as a standard deviation is thus sqrt($M_0$). If the acquisition for a patient yielded $M_0$ counts, and an image is reconstructed from the acquisition, assuming an ideal image formation chain with no error, an image $I_0$ results. A new acquisition with $M_1$ counts results in an image h, and so one. An ensemble of images $I_k$, k=0, . . . , K, is created, where K is the total number of exact repeats of the experiment. The average image $<I_k>_K$, over all K images may be computed. The average image is an approximation of the mean image, which is provided if K approaches infinity. Higher moments, such as the $2^{nd}$ moment, may be computed to obtain the variance of the image. Thus, the mean, which may be unattainable in reality, is somewhere in between average plus or minus the standard deviation sigma with appropriate confidence of about 67% and with about 99% confidence if the error is 3*sigma.

However, it is impractical or impossible to repeat the identical measurement K times, especially for a patient and keeping all other variables constant. To overcome this issue, bootstrapping or binomial subsampling consistent with the Poisson statistics is used to generate K realizations on a computer. One or a few acquisitions from the patient are used to create the simulated data, which is then based on the actual data. Using that simulated data of many sets, a larger image ensemble is created. The image error is estimated as a function of the error associated with measuring a Poisson process.

The known distribution (e.g., in this case Poisson distribution of the isotope decay) is used to simulate different data from one or more actual measures of the data.

In a similar fashion, systematic errors of the measurement system or the data processing may be estimated. $\{\eta_n, n=1 . . . P\}$ is the set of all input parameters defines an image formation model. Only one parameter q is varied at a time, but variation of multiple parameters may be used. The computation may more complicated, but uses the same concept. Within $\eta^{Min}_i < \eta_i < \eta^{Max}_i$, where $\eta^0_i$, denotes the default value, each variation results in a new image $I(\eta_i)$. The set of new images may be compared to $I(\eta^0_i)$. Thus, the systematic error is estimated by perturbing the system matrix or other representation of the image formation model in a known and controlled fashion.

The selection of $\eta_i$ is repeated R times within the given interval and based on an underlying probability distribution that could be uniform or normally distributed. This is akin to the realization in the example of the isotope decay, where the decay has a known distribution (i.e., is a Poisson process). Regardless of the underlying distribution, the resulting image $I_1^{1 \cdots R}$, now form the ensemble for the studying of the input variable $\eta_i$, and thus the moments may be computed, such as average or variance.

This principle applies not only to the error items iii) and iv), but also to i) in the sense that one could also describe distribution probabilities a-priori and compare to reconstructions without it. For instance, a higher probability of uptake or uptake ratio may be assigned in a specific anatomical region, say the heart as compared to the blood pool. Instead of varying the system matrix or the projection operator, a noisy simulated data set is generated. The images resulting from reconstruction of that noisy data set may be compared to images reconstructed from the real data.

The set of all input parameters, $\eta_n$, may include a calibration parameter, injected dose to the patient, injection time, patient weight, patient BMI, and so on. Any parameter used in the image formation model or used to calculate a parameter used in the image formation model may be perturbed. Any parameter that results in differences in the quantitative result may be varied to determine the error information. For instance, error based on SUV values, which is a clinical relevant parameter, are determined. Often, the SUV error depends as much on the entire image formation as on the correct measurement of the patient weight at the time of injection and proper entry. For the remainder of the disclosure, the system matrix is varied as an example of the concept. The parameters $\eta_k$, which are part of the system matrix, are considered. Other parameters of the image formation model may be perturbed and errors calculated instead.

Below, the values of one or more variables of the system matrix are altered and the reconstruction repeated. The differences in the resulting object or image data of the different reconstructions provide systematic error information as a function of location. Depending on the problem, more than one variable may be varied at a time to assess cross-talk and thus correlated errors. The error calculated may be used to identified linked or correlated parameters (e.g., gantry reflection and tilt) and independent parameters, which may then inform subsequent error analysis. All the parameters may be varied given the specific constraints to compute a correlation matrix, and to understand which input parameters highly correlate and which do not. Correlated variables may be treated together in subsequent error analysis. More independent errors may be accumulated with quadrature summation to determine a total error. A multi variate error propagation analysis may be performed given the computed errors.

Localized (e.g., by voxel or other region) error estimation is provided in quantitative functional imaging. By varying one or more aspects of the system matrix or other part of the image formation model used in reconstruction, errors associated with the aspect or aspects in the resulting reconstructed object are determined. The variation in the system matrix may result in different tolerances or errors for different locations, providing the user with localized error information specific to the one or more aspects. The user may identify which aspects lead to greater errors, so focus more on minimizing the source of error (e.g., poor motion correction in x-axis translation).

Figure 1:
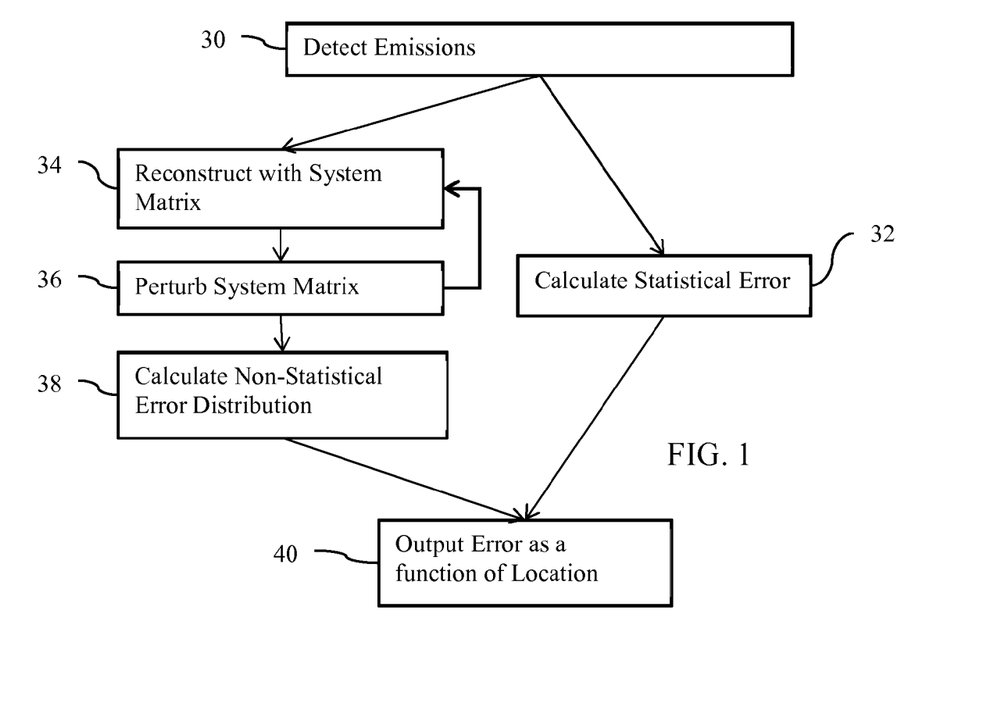
FIG. 1 is a flow chart diagram of one embodiment of a method for estimating error in quantitative functional imaging.

FIG. 1 shows a method for estimating error in quantitative functional imaging. Any functional or nuclear imaging may be used. The discussion below focuses on the system matrix in SPECT. In other embodiments, the method is performed for PET or other imaging modality that measures a value in absolute units. Other aspects of the image formation model may be used, such as biological distribution (e.g., uptake ratio) for perturbing, reconstructing to create an image set (e.g., different reconstruction approaches for different uptake ratios), and error calculation.

Additional, different, or fewer acts may be performed. For example, the calculation of statistical error of act 32 is not performed. As another example, the detection of emissions of act 30 is not performed, but instead previously detected emissions are obtained by data transfer and/or loading from memory. In yet another example, acts for combining different types of error estimates are provided.

The acts are performed in the order shown or a different order. Act 32 corresponds to calculating statistical error and acts 36 and 38 correspond to calculating systematic error. These sets of acts may be performed in parallel, together, or in any order.

In act 30, data representing the patient is obtained. The acquisition of the data is by scanning, such as with an emission tomography system (e.g., PET or SPECT). Emissions are detected with a gamma camera, for example. The acquisition may be by transfer or upload.

The scanning acquires detected emission events for functional information. For PET, each detected emission event corresponds to a line through a patient. For SPECT, the gamma camera obtains signal along a ray from an unknown depth. By detecting emission events from different angles around a patient, a volume may be reconstructed.

For accounting for attenuation, computed tomography (CT) data is also obtained. The acquisition of CT data is by scanning, such as with a CT scanner. Alternatively, the acquisition is by transfer from another source or upload from memory.

In one embodiment, the raw CT data represents projection attenuation values for x-rays. Each attenuation value represents an integration of x-ray attenuation along a line. By acquiring attenuation values for different lines or angles through a patient, attenuation values that may be reconstructed into an object space volume are acquired.

The raw data from the different modalities is acquired with separate scanners, such as CT and PET scanners with different housings or in different rooms. Alternatively, the raw data is acquired with a hybrid system. A collection of emission events and attenuation values from the patient volume are acquired using scanners integrated together in a same housing and/or room. For example, CT and SPECT systems are combined. The combination results in a known spatial relationship of the CT system to the SPECT system. In other embodiments, the spatial relationship is unknown. Calibration, position measurement, and/or feature alignment may be used to define a spatial relationship in other embodiments.

In act 34, the activity concentration (e.g., quantitative SPECT) is reconstructed using a system matrix. An object, distribution of emissions in a volume, or image data is reconstructed from the detected emissions. The quantity or amount of uptake for each location (e.g., voxel) is estimated as part of the reconstruction in computed tomography. The SPECT or other functional imaging system estimates the activity concentration of an injected radio-pharmaceutical or tracer for the different locations. In quantitative SPECT, the goal is to estimate the activity concentration in kBq/ml of the tracer that was injected into and distributed within the patient.

The acquired data is used for reconstruction of an emission tomography representation of the volume in act 34. The reconstruction is iterative and contains a model of the imaging formation physics as a pre requisite of quantitative reconstruction The image formation model includes the detected data (e.g., counts), system matrix, isotope properties, and biology. The isotope properties and biology may be handled in the system matrix. The system matrix represents mechanical property of system, but may include other information (e.g., injection time and patient weight as represented by SUV).

Reconstruction includes a projection operator that is able to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, NNLS, or another approach. For example, one of the reconstructions disclosed in U.S. Pat. No. 8,577,103; 8,350,222, or 8,184,876 is used.

The reconstruction uses a system matrix representing various aspects of the detection of the emissions, including modeling the imaging physics. The imaging physics includes aspects of the SPECT system, such as calibration of the SPECT system. The system matrix includes a model of the collimator allowing for distance dependent point spread function in three-dimensions and thus three-dimensional resolution recovery. For quantitative reconstruction (e.g., estimating activity concentration, such as in Bq/ml), the system matrix also includes within the reconstruction in image space the knowledge of collimator sensitivity, calibration factors, and view time. The variables for these considerations are part of the imaging physics, so are included in the system matrix.

In general, the reconstruction estimates the activity distribution f from projection data g with added noise n, given a system matrix H: Hf=g+n. The image reconstruction is based on the measured image data D and a data model m derived from a reconstructed image object with the help of the system matrix H and a merit function. H is very large matrix, and the inversion in tomography is known as an ill conditioned inverse problem. The inversion in tomography is considered as ill conditioned because small deviations may cause large differences in the result. The inversion process is on noisy data, with a large estimable parameter space and barely sufficient data. Instead of inverting H to $H^{-1}$, the transpose of the system matrix, $H^T$ is used.

The system matrix H is rarely applied directly as a matrix multiplication. Instead, the system matrix is represented as a product of operators $H_n$:

$$H = H_n \otimes \ldots \otimes H_2 \otimes H_1$$

Corresponding to the forward projection, the backward projection from the data space into object space may be described as an application of the transpose $H^T$ of the system matrix H:

$$I_\alpha = \sum_i H_{\alpha i} m_i$$

The transpose $H^T$ is also rarely applied as a matrix multiplication. Instead, it is represented as a product of operators:

$$H^T = H_1^T \otimes H_2^T \otimes \ldots \otimes H_n^T.$$

In general, a forward projection is an application of the system matrix H to an object in object space. The result of a forward projection is a "projected object" in data space. As an example in nuclear imaging, a forward projection is the linear operation that transforms the functional activity density into the total data model $m_i$ of predicted detection events:

$$m_i = \sum_\alpha H_{i\alpha} I_\alpha.$$

Here, i stands for the two-dimensional detection positions on the detector system of the functional imaging system, as well as for the detection time t' and energy E'. $\alpha$ is the voxel or location designation. In general, the detection time and energy of a photon does not need to be the same as the emission time t and energy E. Such cases arise, for example, in PET with time-of-flight corrections, or when the photon energy is changed in a scattering event. In many cases, however, these differences may be ignored, and t'=t and/or E'=E. A photo peak energy window may then include scattered photons, whose estimated contributions $s_i$ are estimated separately.

A data model $m_i$ based on a forward projection and scatter correction may be written as:

$$m_i = \sum_\alpha H_{i\alpha} I_\alpha + s_i.$$

where I is the image and an estimate of the unknown activity distribution f.

Other characterizations and/or approaches for reconstruction may be used. In the reconstruction, the system matrix is used for application of the imaging physics to the detected emissions to create the object or uptake as a function of location in three-dimensions.

For quantitative reconstruction, specific values of the activity concentration are estimated by location. For example, the reconstruction method computes $I_\alpha$ in units of Bq/ml. The values may be a function of various characteristics of the system matrix, such as the amount of attenuation for each of different locations indicated in a Mu map, the registration or alignment (e.g., registration matrix) of the Mu map with the reconstructed object, motion correction, collimator sensitivity, calibration values, view time, or other characteristics. In general, let $H_0$ be the default system matrix, containing relevant parameters from the set $\eta$, defined above. A new matrix $H' = H_0 + H_1$ may be constructed. After reconstruction, $f' = H'^T (g+n)$ represents the estimate based on the modified system matrix.

Quantitative SPECT may compensate for attenuation and scattering. The attenuation map is obtained from CT data, which is registered or spatially aligned to a preliminary SPECT reconstruction. The reconstructed CT volume is used to create a map of attenuation coefficients (Mu map ($\mu$)) as a function of space in three dimensions. The Mu map provides the linear attenuation at each voxel. The CT measures are translated into a Mu map, such as described in U.S. Pat. Nos. 6,950,494 and 7,473,900. The map is the spatial distribution in the volume. The CT information may be used in the emission reconstruction to make the reconstruction better by correcting for the effects of attenuation.

Where an attenuation map is used in the reconstruction, the reconstruction includes refinement of registration between the updated reconstruction of the emission volume and the CT volume. The registration of the reconstructed volume of functional information with a reconstruction of the anatomical information is refined during reconstruction of the emission volume. The translation, rotation, scaling, or combinations thereof are determined for the functional information relative to the anatomical information.

The registration matrix of the system matrix represents the translation, rotation, and/or scale for the alignment of the Mu map and functional imaging reconstructed volumes. For example, the registration matrix incorporates three rotation, three translation, and/or three scaling degrees of freedom for the volumes and/or for each voxel of the volumes. The registration matrix is incorporated in the projections used for reconstructing the volume for the functional information.

For projecting, the system matrix is used to create a data model of the object space volume. The data model is the result of the projection operator applied to the estimated activity concentration, essentially simulating the emission system. Emission reconstruction solves a high dimensional minimization problem, where each voxel is one variable, potentially a $N^3$ matrix, with the goal to minimize some objective function of some distance measure between data and the data model over these variables.

The projection operation includes attenuation, such as the Mu map. The projection operator includes the Mu map, to correctly account for attenuation during the projection of each view. Since gamma rays may be altered by tissue in a similar manner to attenuation of x-rays, the emission events are subject to the anatomical structure represented by the attenuation coefficients. Different voxels or locations attenuate the gamma rays by different amounts.

The registration is combined with the emission reconstruction. The combination includes registration as well as projection for reconstruction in each iteration. The registration is performed as part of the minimization in iterations of the projections. By also allowing minimization over the sixteen or fewer additional parameters of the registration matrix for registration, the initial registration is fine-tuned during each iteration. As the emission image becomes better, the registration becomes better.

The result of reconstruction is an image object representing the functional operation of the patient. The reconstructed volume for emission tomography may be in the form of voxels with intensity values assigned from the data model of the reconstruction. Alternatively, the output is of a projection of the data model onto a viewing or image plane.

The reconstructed volume may include corrections for the attenuation. The registration matrix is used during reconstruction to spatially apply the appropriate attenuation in the correction. The registration matrix is used within the reconstruction for the attenuation correction.

For each location represented by the reconstructed volume, a different or the same error or tolerance occurs. Due to statistical and systematic errors associated with the detected emissions and the reconstruction, different errors may result by location. The errors are of the values of the activity concentration. The errors may be calculated. While the errors are an approximation, the range of error or error bar may indicate the reliability of quantified concentration.

In act 32, the statistical error is calculated. The statistical error is from the Poisson noise. The decay of the tracer creating the emissions is a Poisson variable. The count of emissions at different detectors and view angles may be off due to the statistical error. This random error may manifest as different levels of noise in the activity concentration for different locations in the patient due to the reconstruction.

Any technique for estimating the statistical error in the count levels of emissions may be used. In one embodiment, the statistical error is calculated from a plurality of different realizations of possible statistical errors. A multitude of sample emissions or counts are generated using Bootstrapping or binomial subsampling to create a multitude of noisy realizations. A random number generator or filter following a Poisson or other distribution determines counts to use for each detector and view angle. The detected count is input to the generator, with the output being a randomized value with the Poisson distribution centered over the input value. This process is performed multiple times for each of the counts, resulting is a plurality of different realizations of the possible sets of counts (e.g., detected emissions) used for reconstruction. Noise data $d^r_i$ at the r'th realization and i'th pixel is created.

Using the same process to reconstruct the original data set d, the different r realizations are each reconstructed, providing $l^r_\alpha$. For each location (e.g., voxel or other region), a statistical analysis on the ensemble of $l^r_\alpha$ is performed. For example, the voxel values for each region (e.g., 3×3×3 voxel sub-volumes) are averaged in a given reconstruction, and a statistical value between reconstructions is calculated. Any statistic may be calculated, such as the first and/or second moments (e.g., average and/or variance). The statistical value calculated for each location may be the same or different than for other locations. These statistical values indicate the error induced by the statistical count level present in the detected emission data.

The systematic errors are calculated in act 38. Systematic errors are estimated. The systematic errors represent contribution of error in the physics of the imaging system or other aspects of the image formation model. The error distribution of any systematic source, as discussed above, may be modeled. In one embodiment, the systematic errors are treated as errors occurring as part of the system matrix. Example parameters include calibration, registration, sensitivity, point spread function, attenuation map, or scatter estimate, and injection time. Other aspects of the image formation model may be included in or handled like the system matrix discussion below.

The error is in the resulting quantity of activity concentration as a function of position. The systematic errors are calculated as a distribution of errors in space. Different locations, such as different voxels, may have different maximum error, error distribution, tolerance or other error characteristic than each other. Due to the reconstruction, a same systematic error source and corresponding magnitude may manifest with a different amplitude or other characteristic of error for different locations. For example, the error for one location may be different or the same as the error of another location given a miss-registration by 1 mm along a single vector.

To calculate the systematic errors, the reconstruction is repeated with one or a plurality of different system matrices. The errors are determined from differences in the resulting objects or image data. The one or more objects of one or more reconstructions using different values of the system matrix of act 36 are compared to the object of the reconstruction of act 34 to calculate the systematic error distribution in act 38.

In act 36, the system matrix is altered. The alteration perturbs the values of one or more variables of the system matrix. Based on perturbation theory, the system matrix itself is slightly altered, represented as: $H \rightarrow \tilde{H}$, where $\tilde{H}$ is the slightly perturbed system matrix. In repeating the reconstruction in act 34 with the same emission detections or counts but different system matrix, a perturbed data model $\tilde{m}_i$ is created. The perturbed data model is used to reconstruct a new perturbed image $\tilde{I}_\alpha^r$ or object. Due to tomographic correlation s and the inherent problem of an ill conditioned system, the perturbed image may be quite different than the unperturbed one.

The value or values are perturbed by any amount. Empirical research may indicate how much to perturb a value. For example, a study may determine typical error in calculation of detector sensitivity. This average deviation, deviation at one standard deviation or less, or other derived value may be used.

In one embodiment, the value is perturbed with first order preservation. The amount of change that results in a linear response of the error is used. If a non-linear response to the change occurs, then the larger deviation is not used. A Taylor expansion may be used to determine the linearity of response. If the calculated error is beyond a linear response, then the adjustment may not be used. This amount of adjustment is informed by the response using the gathered data and particular system matrix and reconstruction rather than a pre-determined empirical value. In other embodiments, the amount of adjustment applied using first order preservation is pre-calculated for a given functional imaging system or type of system.

Any aspect of the system matrix may be perturbed. For example, the attenuation map, registration of the attenuation map to the functional object, calibration values, motion correction, collimator sensitivity, point spread function, view time, or combinations thereof may be altered. Any variable of these aspects may be changed. For example, motion correction and/or registration are represented by translation along three axes, rotation about the three axes, and scale. Any one or more (e.g., all seven) of these variables may be used, such as adding a 1 mm shift in the x-axis translation. Others or none of the variables are not perturbed, such as only altering translation and not rotation or scale.

In one embodiment, the attenuation map of the system matrix is altered. The attenuation map indicates the amount of attenuation for each type of tissue and/or for each voxel or region. For example, one value of attenuation is used for soft tissue locations and a different value of attenuation is used for bone. Any gradations or resolutions in types of tissue and corresponding different attenuation values by type may be used. Only the soft tissue, only the bone, two or more, or all of the attenuation values for the different types may be perturbed. For example, the attenuation map is obtained using CT measures, such as obtaining with a conversion taught in U.S. Pat. No. 6,950,494. This conversion or attenuation map is a reference Mu map. The map is then perturbed, such as altering the soft tissue value up or downwards in magnitude, or a value used to derive the map is perturbed, such as altering by 2% when estimating the effective transmission energy. This change creates a Mu map that is similar to the reference Mu map, but has one or more different values. Reconstruction in act 34 with such a Mu map may be used to find the error resulting from such miss-estimation in attenuation.

In another embodiment, the registration of the attenuation map with the functional imaging object is altered. One or more variables of the alignment of the attenuation with the functional imaging system are altered in act 36. For example, a value in the registration matrix used to begin or initialize the reconstruction is changed. The attenuation map is slightly miss-registered, such as changing the translation, rotation, or scale along one or more axes, to assess the resulting impact. Motion correction to deal with patient motion (e.g., breathing) may alternatively or additionally be altered.

In yet another embodiment, one or more aspects of the collimator sensitivity or point spread function are altered. For example, the point spread function used for one or more detectors is perturbed in some way, such as altering a peak, fall-off, or other characteristic. Calibration and/or view time variables may likewise be altered. Any aspect of the system matrix is altered.

After alteration in act 36, the reconstruction of act 34 is repeated. The object is reconstructed from the detected emissions, but with the altered system matrix. The same type of reconstruction is used, but with one or more changes to the system matrix for measuring error. The other components of the reconstruction remain the same. For example, the reconstructing is performed with the altered attenuation map, registration, motion correction, collimator sensitivity, calibration factors, and/or view time in the system matrix.

The objects or image data from the reconstruction without perturbing and from the reconstruction with perturbing are compared to find the resulting error as a function of location in act 38. Rather than relying on one alteration, the altering and reconstructing with the perturbed system matrix may be repeated multiple times. For example, a value of a given variable of the system matrix is changed for each repetition (e.g., 1 mm, 2 mm, 3 mm, and then 4 mm translation miss-registration in a sequence or parallel processing of four alterations. Any number of alterations, step sizes, variation in step sizes, or range of alteration may be used. A different change to the system matrix is provided for each repetition. In each repetition, the value for the same variable is changed (e.g., soft tissue attenuation).

In an alternative or additional embodiment, the repetition of acts 36 and 34 is for different variables. Different variables of a same aspect of the system matrix are perturbed. For example, one or more values for soft tissue are used as well as one or more values for bone or other tissue. As another example, values for translation along two or more axes are perturbed. In another example, translation and rotation values are perturbed. The reconstruction is repeated for each of the alterations (e.g., a separate reconstruction for each value of each of the variables) or different combinations of the alterations.

In an alternative or additional embodiment, variables for different aspects of the system matrix are perturbed. For example, both registration and attenuation variables are perturbed. Any combination of two or more aspects may be altered. Only one, two, or more variables of each aspect are altered. The correlation of different variables with each other may be calculated from the results.

For any given repetition, only one value is altered. Another value or the same value is the only value altered in a subsequent repetition. The various alterations are performed sequentially. Alternatively, parallel processing is performed allowing the alterations to be performed separately but at a same time. In another embodiment, two or more alterations to the system matrix are performed for a given repetition of the reconstruction. For example, translation along two axes is miss-registered in one alteration, and one reconstruction is performed with the system matrix having both alterations. Any combination of two or more variables being altered for a given repetition may be used.

In another embodiment, the different realizations from the statistical error calculation are used. A given altered system matrix is applied to each of the detected emission realizations. The reconstruction of act 34 is repeated multiple times for one alteration of the system matrix in act 36 using the different detected emission realizations. The system matrix may be altered multiple times with a resulting multiple reconstructions for each of the alterations.

As a result of performing acts 36 once or performing a plurality of repetitions, two or more reconstructed objects or corresponding image data sets are created. Each reconstruction represents the same locations. An activity concentration value for a given location is provided by each of the reconstructed objects. For example, with two repetitions, three values for each location are provided. For each location, the same or different values (e.g., activity concentrations) may be provided. For example, one voxel may have two different values (e.g., 20, 20, and 21 kBq/ml) from three reconstructions, another voxel may have three different values (e.g., 20, 24, and 21 kBq/ml) from the three reconstructions, and yet another voxel may have one value (e.g., 20 kBq/ml for all three) from the three reconstructions. In this fashion and in conjunction with multiple repetitions, a set of images $^{\epsilon}\tilde{I}_{\alpha}^{r}$ for various errors epsilon $\epsilon$ is provided.

In act 38, the systematic error is calculated. A difference between the reconstruction from estimating with and without the altered system matrix or matrices is calculated. For example, the average, variance, or other statistic is calculated for each location or region of multiple locations.

In one embodiment, the calculation is a mere difference operation. For example, a difference between the object (i.e., activity concentration) reconstructed with the original system matrix and one or more objects (i.e., activity concentrations) reconstructed with altered system matrices is calculated. The resulting error data may be represented as an error image. Given a simple case of two reconstructed objects (one error or alteration $\epsilon$), the error image is represented as a variance: $^{\epsilon}Y = I_{\alpha}^{r} - ^{\epsilon}\tilde{I}_{\alpha}^{r}$. The same representation may be used where E represents an error vector or matrix of multiple alterations.

In other embodiments, functions other than a mere difference are used. Any norm may be used to generate the variance (e.g., $^{\epsilon}Y = (I_{\alpha}^{r}, ^{\epsilon}\tilde{I}_{\alpha}^{r})$) or other measure of error. Any statistical information from the different values for a given location may be calculated from the available reconstructed objects. In one embodiment, a maximum error between the estimated activity concentration without the perturbation and with the different changes is calculated. Differences between the reconstruction without the alteration and each of the reconstructions with different alterations are calculated. From the set of differences for a location, the maximum error or difference within a linear response range of the errors is selected. The maximum error without consideration for the linearity or not of the differences may be selected.

In an example using an attenuation or registration alteration, the true reference Mu map and/or registration is not known. In general, the system model is a model with some estimated error. For each specific assumption, a maximum error range is created, that is then probed by itself or in combination with other errors and resulting in a multitude of images, which for instance show the range of deviation from the reference or assumed best model. The maximum error from the likely possibilities is selected as the error.

One or both statistical and systematic errors may be calculated. In one embodiment, the error is calculated from objects reconstructed both with different realizations and the different system matrix perturbations. Each system matrix alteration is used to separately reconstruct for each of multiple realizations of the detected emissions, resulting in a plurality of reconstructed objects. The errors for the different locations are calculated from the reconstructed objects so include both statistical and systematic error.

In another embodiment, the statistical and systematic errors are calculated separately. Addition, multiplication, weighted multiplication, or other combination of the two errors for each location is used to create a combined error. Any error propagation may be used, such as adding errors in quadrature. Alternatively, the errors are maintained separate.

In act 40, the error or errors are output. The systematic error, an error including systematic and statistical noise, or separate systematic and statistical errors are output. For example, one error metric (e.g., value) that is a function of both sources of noise is output.

The output may transmitted, such as over a network. The output may be stored in a memory. Any output may be provided.

The errors are output for different locations. In one embodiment, the output is a map showing the systematic errors as a function of location. The errors are calculated at any resolution, such as separate errors for each voxel in a three-dimensional volume, errors for different regularly spaced multi-voxel regions, or errors for each type of tissue (e.g., organ, tumor, or other region identifier). This set of errors by location is a map.

The map of errors is used to generate an image. The image may be of an arbitrary plane through a volume, such as interpolating the errors to a plane in a multi-planar reconstruction. Cross sections of the volume may be mapped to display values. The image may be a projection rendering from a given view direction, such as applying opacity and summing the errors along view lines. The image may be any three-dimensional rendering, such as a surface or projection rendering. In one embodiment, CT data or the functional image reconstruction is used to identify one or more regions of interest and the image of errors is formed to highlight (e.g., more opaque) the regions of interest.

The image shows the error distribution. The errors are mapped to an intensity, color, brightness or other characteristic. The image may include other information, such as functional and/or CT information. For example, a gray scale CT image has color information mapped from functional information. The error modulates the brightness, hue, or other characteristic of the color. Any functional, anatomical, or functional and anatomical imaging may be used. Alternatively, a separate error image is generated and displayed adjacent to or sequentially with the functional image. Since different errors may be provided for different locations, the image represents the distribution of errors with in the volume of the patient.

In other embodiments, the error is displayed as text for any selected locations. For example, a mouse over display is provided. Other techniques for communicating the error as a function of location may be used.

Figure 2:
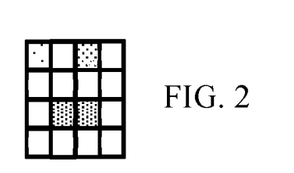
FIG. 2 is an example image showing systematic error as a function of location.

FIG. 2 is a simplified example of an error image. Sixteen separate regions are shown. Each region is a voxel, group of voxels, or other region (e.g., organ, tissue type, or segmentation). While shown as uniform in size and shape, the sizes and/or shapes of the different regions may vary. Four different error magnitudes, ranges, or other characteristic are shown. The different dot patterns represent different errors. The distribution of errors is shown with different amounts of error in some regions as compared to other regions. Some regions have the same amount of error.

The same source or sources of error lead to this distribution. For example, the soft tissue attenuation value is changed in the system matrix. Due to the reconstruction with a specific set of detected emissions, the error for some regions is greater than for others. These regions may or may not correspond to soft tissue locations.

Figure 3:
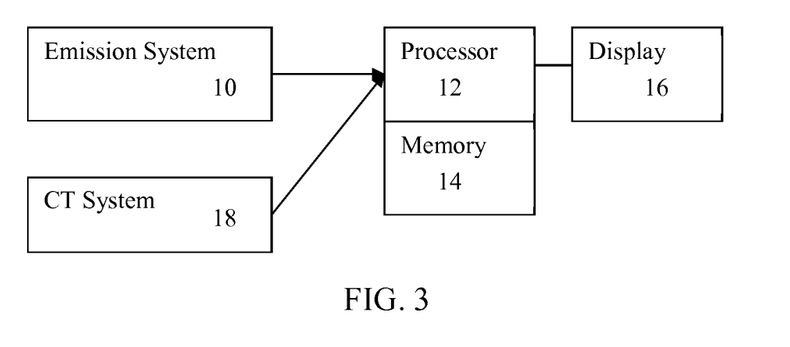
FIG. 3 is a block diagram of a system, according to one embodiment, for estimating error in quantitative functional imaging.

FIG. 3 shows a system 10 for estimating error in quantitative functional imaging. The system 10 includes an emission system 10, a computed tomography system 18, a processor 12, a memory 14, and a display 16. The processor 12, memory 14, and/or display 16 are part of the emission system 10, part of the CT system 18, or are separate (e.g., a computer or workstation). Additional, different, or fewer components may be provided. For example, the system is a computer without the emission system 10 or the CT system 18. As another example, the system 10 includes a magnetic resonance system in addition to or as a replacement for the CT system 18. In yet another example, the CT system 18 is not provided. Other parts of the system may include power supplies, communications systems, and user interface systems.

The emission system 10 is a PET, SPECT, or other nuclear imaging system. As a PET system, a detector array of scintillation crystals coupled to avalanche photo diodes or photomultiplier tubes is in a ring around a patient. The detectors are arranged individually or in groups. The detectors generate three analog signals, two position signals and one energy signal. Other formats may be provided. The signals from the detectors are processed to identify specific events. The timing and location information are used to determine the existence of a valid event (i.e., positron emission) and the location of the event (e.g., line along which the event occurred).

As a SPECT system, one or more gamma cameras are connected with a gantry. The gamma cameras rotate about the patient. The emission events are detected with the camera at different position or angles relative to the patient.

The CT system 18 includes an x-ray source and detector connected to a gantry. The gantry moves the x-ray source and detector around the patient to scan. The same or different gantry may be used with the gamma camera of the SPECT system.

In one embodiment, the emission system 10 and the CT system 18 are in a same room with a shared patient bed. A robot or track guides the bed to position the patient in the desired system for scanning at a given time. In another embodiment, the emission system 10 and the CT system 18 share a same housing in a hybrid system. The patient is positioned in a bore or on a bed. Both systems 10, 18 are arranged to scan the patient while the patient is in the same general position, either sequentially or simultaneously.

The detected attenuation, emission events, other anatomical information, other functional information, or other scan data is stored in the memory 14. The data is stored in any format. The memory 14 is a buffer, cache, RAM, removable media, hard drive, magnetic, optical, database, or other now known or later developed memory. The memory 14 is a single device or group of two or more devices. The memory 14 is part of emission system 10, the CT system 18, or a remote workstation or database, such as a PACS memory.

The emission system 10 is configured to reconstruct the imaged volume by applying a system matrix to the detected data. Any reconstruction may be used. The processor 12 is used to perform the reconstruction or the emission system 10 has another processor that performs the reconstruction. The emission system 10 accesses the detected emission events from the memory 14 to reconstruct.

The memory 14 may store data at different stages of processing, such as raw data representing detected events without further processing, filtered or thresholded data prior to reconstruction, reconstructed data, filtered reconstruction data, system matrix, data model, projection data, thresholds, an image to be displayed, an already displayed image, or other data. The memory 14 or a different memory stores data used for processing, such as storing a table of alterations of the system matrix for calculating error and/or the data. For processing, the data bypasses the memory 14, is temporarily stored in the memory 14, or is loaded from the memory 14.

The memory 17 is additionally or alternatively a non-transitory computer readable storage medium with processing instructions. The memory 14 stores data representing instructions executable by the programmed processor 12. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions, such as one processor (e.g., application specific integrated circuit or field programmable gate array) for reconstructing and another for perturbing the system matrix and/or calculating error. In one embodiment, the processor 12 is a control processor or other processor of emission system 10 or the CT system 18. In other embodiments, the processor 12 is part of a separate workstation or computer.

The processor 12 operates pursuant to stored instructions to perform various acts described herein, such as reconstructing, altering a system matrix (e.g., looking up one or more alterations from a table), calculating statistical error, calculating systematic error, and/or generating an error image. The processor 12 is configured by software and/or hardware to perform, control performance, and/or receive data resulting from any or all of the acts of FIG. 1.

In one embodiment, the processor 12 is configured to vary a value of one or more variables of the system matrix or other aspect of the image formation model and calculate systematic errors as a function of location from outputs of the reconstructions with the various values. Where the processor 12 is also configured to perform the reconstructions, parallel processing may be used, such as with a graphics processing unit. Since reconstruction is computationally intensive, various error segments may be estimated in parallel. Where the processor 12 is configured to generate a plurality of realizations for calculating statistical error as well, parallel processing with multiple devices may allow for error calculation within minutes of completion of a scan of a patient.

The display 16 is a CRT, LCD, plasma screen, projector, printer, or other output device for showing an image. The display 16 displays an image of the reconstructed functional volume and/or anatomical volume. Error information may be separately displayed. For example, text representing a characteristic of the error (e.g., error range or error bar) is displayed where the user selects a location or positions a pointer at the location. As the point is repositioned, the corresponding error information is provided. As another example, an error image is generated. The display 16 may display a value, graph, notation, annotation or other information calculated using the errors as a function of space.

Images for different sources and/or magnitudes of the sources of error may be generated. The user may determine which potential source of error or sources of errors are most important relative to the resulting distribution of errors from reconstruction and spend a more focused effort on controlling those sources relative to other sources during scanning. The user may make more informed choices using functional imaging information based on the possible error, regardless of the source or in view of particular sources of error.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for estimating error in quantitative functional imaging, the method comprising:
    estimating, with a functional imaging system, activity concentration as a function of locations of an injected radiopharmaceutical in a patient;
    calculating, with a processor, systematic errors of the activity concentration as a function of the locations for the patient, the systematic error for at least one location different than the systematic error for another location; and
    outputting the systematic errors.

2. The method of claim 1 wherein estimating comprises reconstructing the activity concentration as a function of a system matrix, and wherein calculating the systematic errors comprises perturbing the system matrix and performing the reconstructing using the perturbed system matrix.

3. The method of claim 2 wherein perturbing comprises perturbing with first order preservation.

4. The method of claim 3 wherein perturbing comprises perturbing by an amount in a linear response range.

5. The method of claim 2 wherein perturbing the system matrix comprises altering an attenuation map of the system matrix, and wherein performing comprises performing the reconstructing with the altered attenuation map.

6. The method of claim 2 wherein perturbing the system matrix comprises altering registration of an attenuation map of the system matrix, and wherein performing comprises performing the reconstructing with the altered registration.

7. The method of claim 2 wherein perturbing the system matrix comprises altering motion correction of the system matrix, and wherein performing comprises performing the reconstructing with the altered motion correction.

8. The method of claim 2 wherein perturbing the system matrix comprises altering collimator sensitivity of the system matrix, and wherein performing comprises performing the reconstructing with the altered collimator sensitivity.

9. The method of claim 2 wherein perturbing the system matrix comprises altering calibration factors of the system matrix, and wherein performing comprises performing the reconstructing with the altered calibration factors.

10. The method of claim 2 wherein perturbing the system matrix comprises altering view time of the system matrix, and wherein performing comprises performing the reconstructing with the altered view time.

11. The method of claim 2 wherein the perturbing and performing are repeated with different changes to the system matrix, and wherein calculating comprises identifying a maximum error between the estimated activity concentration without the perturbation and with the different changes.

12. The method of claim 1 wherein calculating the systematic errors comprises calculating systematic errors due to physics of the functional imaging system.

13. The method of claim 1 wherein calculating comprises determining a difference between a reconstruction from the estimating and a reconstructing with the system matrix altered.

14. The method of claim 1 wherein outputting the systematic errors comprises outputting a map showing the systematic errors as a function of the locations.

15. The method of claim 1 wherein outputting comprises outputting an image representing distribution of the systematic errors in a region of the patient.

16. The method of claim 1 further comprising determining statistical errors in count levels, wherein outputting comprises outputting an error metric that is a function of the statistical errors and the systematic errors.

17. The method of claim 16 wherein calculating the systematic errors comprises calculating for a plurality of realizations of the statistical errors.

18. In a non-transitory computer readable storage medium having stored therein data representing instructions executable by a programmed processor for estimating error in quantitative functional imaging, the storage medium comprising instructions for:
   first reconstructing an object from detected emissions in nuclear imaging as a function of a system matrix;
   altering the system matrix;
   second reconstructing the object from the detected emissions as a function of the altered system matrix;
   calculating a distribution of errors for at least two locations in space as a function of a difference of the object of the first reconstructing and the object of the second reconstructing, the error for one a first of the locations being different than for another a second of the locations; and
   generating an image of the distribution of the errors.

19. The non-transitory computer readable storage medium of claim 18 wherein altering comprises perturbing an attenuation map, a registration, a calibration, a motion correction, a collimator sensitivity, a view time, or combinations thereof of the system matrix;
   further comprising repeating the altering and second reconstructing for different alterations of the system matrix; and
   wherein calculating comprises calculating as a function of differences of the object of the first reconstructing with the objects of the repetitions of the second reconstructings.

20. A system for estimating error in quantitative functional imaging, the system comprising:
   a single photon emission computed tomography scanner configured to reconstruct with an image formation model and detected data;
   a processor configured to vary a value of one or more variables of the image formation model and calculate systematic errors as a function of location from outputs of reconstructions with the image formation model with the various values of the one or more variables.

\* \* \* \* \*